United States Patent [19]

Kuni et al.

[11] Patent Number: 4,647,196

[45] Date of Patent: Mar. 3, 1987

[54] SURFACE FLAW DETECTION METHOD

[75] Inventors: Asahiro Kuni, Tokyo; Kazuo Yamaguchi, Sagamihara; Nobuyuki Akiyama, Yokohama; Juro Endo, Kumagaya, all of Japan

[73] Assignee: Hitachi Metals, Ltd., Tokyo, Japan

[21] Appl. No.: 695,231

[22] Filed: Jan. 28, 1985

Related U.S. Application Data

[63] Continuation of Ser. No. 340,658, Jan. 19, 1982, abandoned.

[30] Foreign Application Priority Data

Jan. 20, 1981 [JP] Japan ................................. 56-5941
Jan. 20, 1981 [JP] Japan ................................. 56-5942

[51] Int. Cl.$^4$ .................... G01N 21/88; G01B 9/02
[52] U.S. Cl. ..................................... 356/237; 356/359
[58] Field of Search ............. 356/353, 357, 354, 369, 356/237, 239

[56] References Cited

U.S. PATENT DOCUMENTS

| 2,743,645 | 5/1956 | Larsson et al. | 356/359 |
| 3,720,471 | 3/1973 | Kasahara et al. | 356/357 |
| 4,302,108 | 11/1981 | Timson | 356/359 |

FOREIGN PATENT DOCUMENTS 1502280 10/1967 France ............................. 356/357

OTHER PUBLICATIONS

King et al., "A Comparison of Methods for Accurate Film Thickness Measurement", *J. Phys. E.*, vol. 5, No. 5, pp. 445–449, May 1972.
Bruce et al. "Relative Flatness Measurement of Uncoated Optical Flats", *Applied Optics*, vol. 14, No. 12, pp. 3082–3085, Dec. 1975.
Kwon, "Infrared Lateral Shearing Interferometers", *Applied Optics* vol. 19, No. 8, pp. 1225–1227, Apr. 1980.

*Primary Examiner*—David C. Nelms
*Assistant Examiner*—Matthew W. Koren
*Attorney, Agent, or Firm*—Antonelli, Terry & Wands

[57] ABSTRACT

A flaw detection method for detecting flaw existing in the surface of a substantially plate-shaped examination object by making use of an interference of light. A coherent light is applied to the surface of the examination object and also to a reference mirror surface. The light reflected by the surface of the examination object and the light reflected by the reference mirror surface are made to interfere with each other to form an interference image from which the flaw is detected. The reference mirror surface is disposed at an optical inclination to the surface of the examination object. The reference mirror surface may be the reverse surface of the examination object while the obserse side of the same is being examined. Infrared coherent ray is preferably used as the coherent light.

4 Claims, 12 Drawing Figures

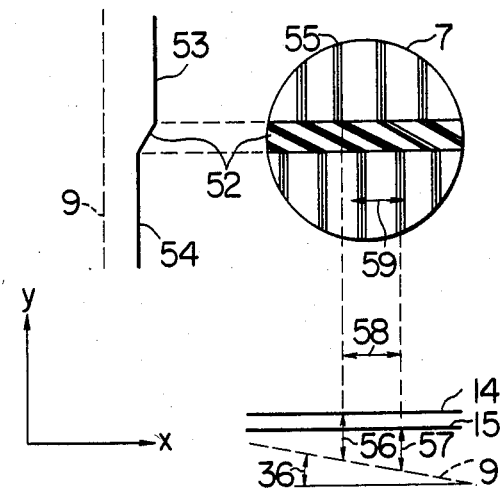
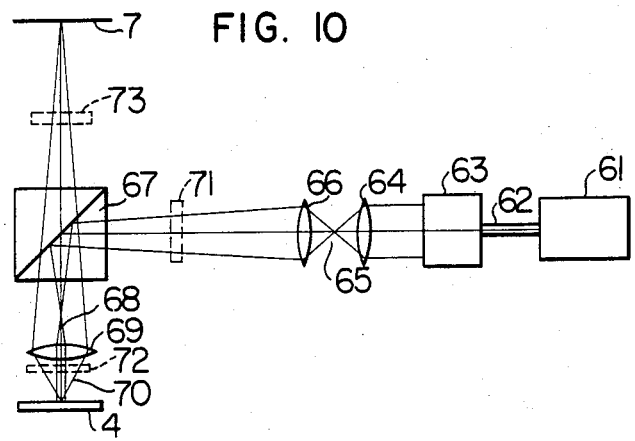
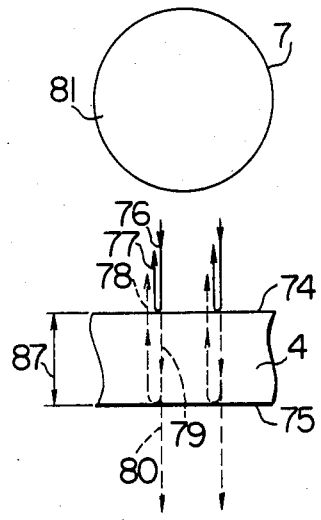
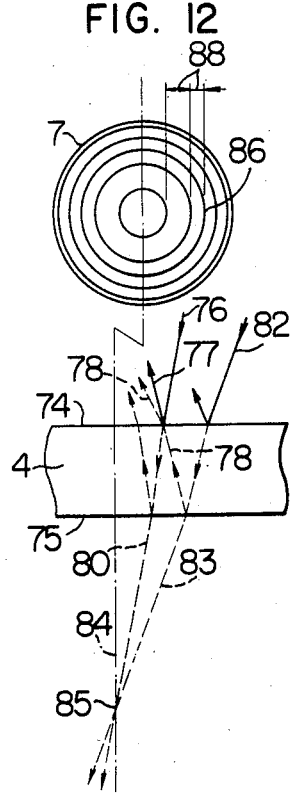

SURFACE FLAW DETECTION METHOD

This is a continuation of application Ser. No. 340,658 filed Jan. 19, 1982.

BACKGROUND OF THE INVENTION

The present invention relates to a flaw detection method for detecting any trace of a flaw in the surface of an examination object by making use of an interference of light.

BRIEF DESCRIPTION OF THE DRAWINGS

FIGS. 8 and 9 illustrate the principle of flaw detection method of the invention using interference of light;

FIG. 10 is an illustration of an optical system in accordance with an embodiment of the invention; and FIGS. 11 and 12 show the principle of interference in accordance with the invention.

DESCRIPTION OF THE PRIOR ART

Figure 1:
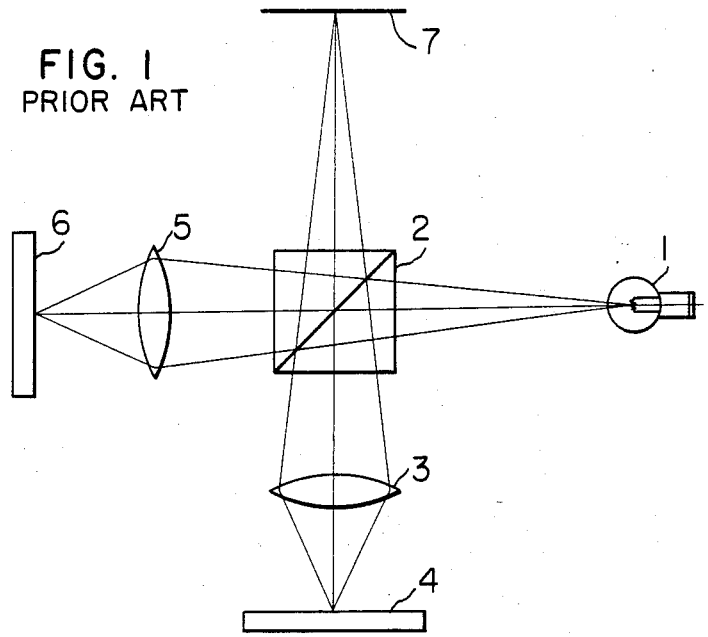
FIG. 1 is an illustration of an example of an interference optical system.

FIG. 1 diagrammatically shows an example of an interference optical system for obtaining an interference image of the surface of the examination object. The system has a coherent light source 1 adapted to emit a light such as laser beam. The light is split into two beams by means of a beam splitter 2. One of the light beams is projected on the surface of the examination object through an objective lens 3, while the other light beam is projected on a reference mirror 6 through an objective lens 5 which usually has a magnification equal to that of the objective lens 3. The reference mirror 6 is a mirror having a mirror surface of a high precision of flatness in the field of vision of the objective lens 5. The light reflected by the examination object 4 and the light reflected by the reference mirror 6 are focussed by the objective lenses 3 and 5, respectively, and are superposed together through the beam splitter 2 so as to form an interference image on an image surface 7.

The principle or theory of interference can be explained by folding back the Figure along the line showing the reflecting surface of the beam splitter 2 so as to superimpose the virtual image of the reference mirror 6 to the surface of the examination object 4.

Figure 2:
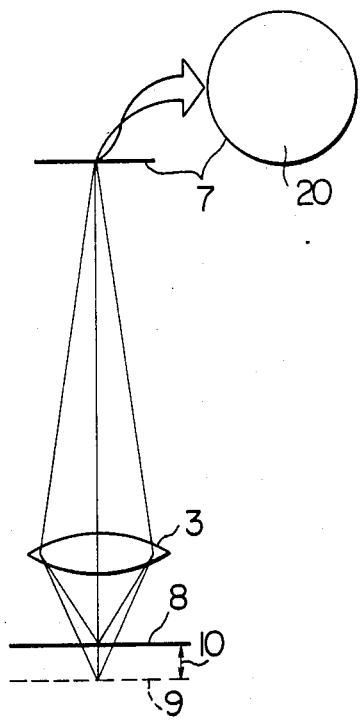
FIG. 2 is an illustration of the principle of interference of light.
Figure 3:
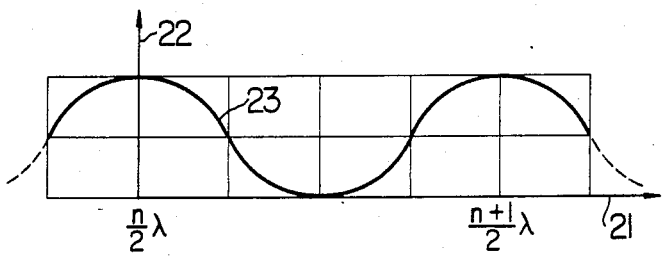
FIG. 3 is a diagram showing the change of interference intensity.

FIG. 2 illustrates the virtual image 9 of the reference mirror surface by broken line. An assumption is made here that the surface 8 of the examination object and the virtual image 9 of the reference mirror surface are perfectly in parallel with each other. If the distance 10 therebetween is n times as large as a quarter ($\frac{1}{4}$) of the wavelength λ of the light used, both light beams act to negate each other by interference, provided that n is an odd number. Therefore, a uniform image 20 of a dark interference intensity is formed on the image surface 7. However, provided that n is an even number, the reflected light beams act to strengthen each other, so that a uniform image of bright intensity is formed on the image surface 7. Namely, the image surface is repeatedly and alternatingly brightened and darkened as the reference mirror is moved in the direction of the optical axis. The brightness of the image surface 7 takes the maximum value at each time the distance amounts to a length which is n' (an integer) times as large as $\frac{1}{2}.\lambda$. FIG. 3 shows this change of brightness, representing the change in the distance by axis of abscissa and representing the interference intensity 22 by the axis of ordinate. The change in the brightness is shown by a curve 23.

With this knowledge of characteristics of interference, a discussion will be made hereinunder as to how these characteristics are applied to the detection of a trace of a flaw on the examination object, with specific reference to FIG. 4. It is assumed here that the surface 8 of the examination object presents a background 24 which contains a trace of a flaw 25 recessed from the level of the background 24. Supposing that the depth 26 of this flaw 25 amounts to $\frac{1}{8}.\lambda$, an intensity of interference between the backgrounds 24 and the flaw 25 is obtained as shown by the graph in FIG. 5. Namely, the change of brightness of the background 24 takes the maximum value as shown by full-line curve 27 at each time the distance 21 takes a value represented by $\frac{1}{2}.n.\lambda$ (n being a positive integer), as in the case of characteristics shown in FIG. 3. On the other hand, the change of brightness of the flaw 25 is changed at a phase delay of $\frac{1}{8}.\lambda$ from the change of brightness of the background 24, as indicated by broken-line curve 28.

Figure 5:
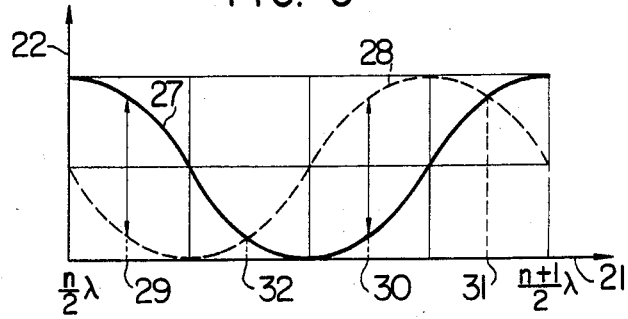
Figure 6:
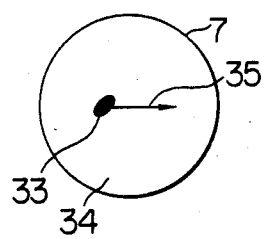

For a clear recognition of the flaw 25, it is necessary to obtain a distinctive difference between the brightness of the background 24 and the brightness of the flaw 25, i.e. a contrast of the flaw 25 in relation to the background 24. The graph of FIG. 5, therefore, shows that the contrast is changed as the distance 21, which is the essential requisite for the interference, is changed. There are two points of distance 21 where the difference of brightness between the background 24 and the flaw 25, i.e. the contrast of the flaw 25, is maximized. These points are designated at numerals 29 and 30. The distance 29 presents, as shown in FIG. 6, a dark interference image 33 of the flaw 25 in the bright interference image 34 of the background 24, on the image surface 7. At the distance 30, although not shown, the relation of brightness between these images is inversed. As the examination object is moved or as a result of scanning of the reflected light or interference image (these actions will be generally referred to as "movement or scanning", hereinunder), the interference image 33 of the flaw 25 having a high contrast moves across the image surface 7, so that the flaw can be detected easily.

Figure 7:
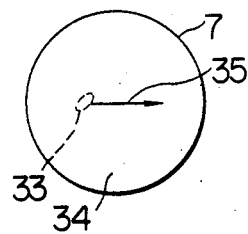

However, in the case where the distance as indicated at 31 or 32 is taken, there is no difference in the brightness between the background 24 and the flaw 25. For instance, as shown in FIG. 7, the interference image 33 of the flaw 25 has no contrast to the interference image 34 of the background, at the distance 31, so that it is impossible to detect the flaw 25. This point is a fundamental defect of the interference type flaw detection method. This problem can occur for every flaw having a height difference smaller than $\frac{1}{4}.\lambda$ from the background level.

Namely, there is no optimum value for the distance, unless the height difference of the flaw from the background is constant, even though the vibration on the reference mirror and the examination object is completely eliminated and even if the distance could be controlled finely on the order of tens of hundredth of the wavelength following up minute undulation of the surface of the examination object. It is, therefore, impossible to perfectly eliminate the overlooking of an existing flaw.

SUMMARY OF THE INVENTION

Accordingly, an object of the invention is to provide a flaw detection method using interference of light, capable of detecting an existing trace a flaw without overlooking the same, thereby to overcome the above-described problems of the prior art.

To this end, the present invention proposes to make a positive use of an interference fringe. Namely, it is intended to provide an arrangement such that at least a pair of interference fringes appears in the detection range and that the condition of interference can be differentiated in this detection range.

More specifically, according to the invention, there is provided a surface flaw detection method in which coherent light is applied to the flat surface of an examination object and to a reference mirror surface, and the light reflected from the examination object and the light reflected from the reference mirror surface are made to interfere, so that a flaw existing in the surface of the examination object is detected through the interference image, characterized in that the reference mirror surface is optically inclined relatively to the surface of the examination object to provide interference fringes.

The above and other objects, features and advantages of the invention will become clear from the following description of the preferred embodiments taken in conjunction with the accompanying drawings.

DESCRIPTION OF THE PREFERRED EMBODIMENTS

EMBODIMENT 1

Figure 8:
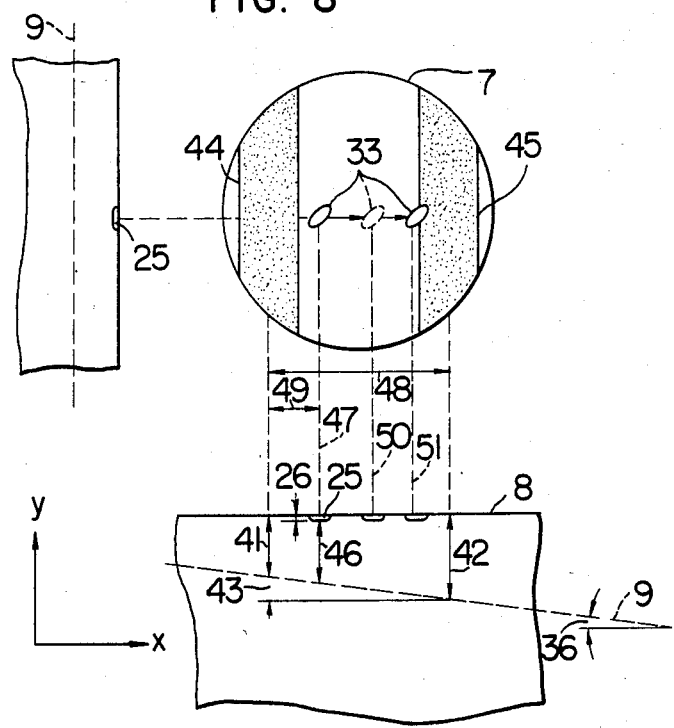

According to the invention, the reference mirror is mounted at an inclination, in order to ensure the production of at least a pair of interference fringes, i.e. at least one bright fringe and at least one dark fringe. Referring to FIG. 8, the direction of movement or scanning is indicated by x. The reference mirror is positioned in parallel with the surface 8 of the examination object in the direction y, but is inclined at an angle 36 in the x direction as illustrated. By so doing, a dark interference fringe 44 is formed at the position of distance 41 where the light reflected from the examination object surface 8 and the light from the virtual image 9 on the reference mirror surface 9 act to negate each other. Also, an interference fringe 45 is formed at the position of distance 42 spaced by a length 43 corresponding to $\frac{1}{2}.\lambda$ from the position of distance 41.

As the flaw 25 is moved in the x direction, i.e. from the left to the right across the surface image 7 as a result of the movement or scanning, the interference image 33 of the flaw 25 comes to take the same level of brightness as the interference fringe 44, i.e. most darkened, at a position 47 where the distance 46 between the bottom surface of the flaw 25 and the virtual image 9 of the reference mirror surface is equal to the distance 41. Provided that the depth 26 of the flaw 25 equals to $\frac{1}{8}.\lambda$, the position 47 is shifted to the right from the position of the interference fringe 44 by a distance 49 which is $\frac{1}{4}$ of the distance 48 between two interference fringes 44 and 45, because this distance 48 represents the height differential of $\frac{1}{2}. \lambda$.

Figure 4:
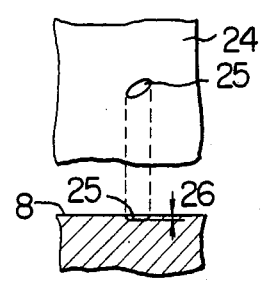
FIGS. 4 to 7 show how a flaw is detected by means of an interference image.

As the flaw 25 is moved, the contrast of the flaw 25 is gradually decreased and nullified at the position 50, as will be easily imagined from FIG. 4. In this position, therefore, the flaw 25 cannot be recognized. As the flaw 25 is moved further, however, the contrast starts to increase again, and is maximized at the position 51. Namely, at this position 51, the flaw 25 is brighter than the background, on the contrary to the position 47.

By varying the condition of interference along the direction of movement or scanning, it is possible to impart a contrast to the flaw depending on the position. The position of the greatest contrast is determined by the amount of depth or height of the flaw. However, if it is arranged, such that at least a pair of interference fringes including bright and dark fringes are produced in the range detectable by the detector (within the image surface in the case of visual check), it is possible to obtain one or two points without fail where the contrast is maximized. It is, therefore, possible to detect the flaw without overlooking the same.

It does not matter that the interference fringes are formed obliquely due to a difference in the interference condition in the direction perpendicular to the direction of movement or scanning. This occurs when the reference mirror is inclined in the direction y or when an inclination in the direction y is caused due to an undulation of the surface of the examination object. This, however, does not cause any substantial problem provided that the reference mirror is beforehand adjusted such that at least a pair of interference fringes are produced in the direction of movement or scanning over the entire region of examination.

As will be understood from the foregoing description, the flaw detecting method of this embodiment ensures a highly reliable flaw detection by avoiding the possibility of overlooking a flaw attributable to insufficient contrast which is the fundamental defect of the interference flaw detection method, without being accompanied by any deterioration of detection sensitivity inherent in the interference flaw detection method.

FIG. 9 shows a case where a minute step is formed on the surface of the examination object. Namely, the surface 8 of the examination object has a higher surface 53 and a lower surface 54 demarked by a step 52. The reference mirror is inclined in the x direction by a predetermined amount but is not inclined, i.e. it is held in parallel with the higher and lower surfaces 53, 54, in the y direction, relatively to the examination object surface 8. By so doing, the interference fringe 55 appearing in the image surface 7 appears as two offset lines corresponding to the higher and lower surfaces 53 and 54 connected by an oblique line corresponding to the step 52. The division of a single interference fringe into two offset lines means that the distance 56 of the higher surface 53 at the position of the interference fringe equals to the distance 57 of the lower surface at the position of the interference fringe. It is, therefore, possible to determine the height of the step 52, in terms of a multiple of $\frac{1}{2}.\lambda$, provided that the amount of the offset 58 is known as a multiple of the distance 59. Also, whether the step is upward or downward can be determined by discriminating whether the interference fringe is offset to the left or right. If it is desired to know merely the presence of the minute height distance such as a flaw, the detection of such a flaw can be made at a distinctive contrast, because the interference intensity is changed at the portion of such a flaw as compared with the portion around the flaw.

EMBODIMENT 2

FIG. 10 shows an optical system in which the light reflected from the observe side of the examination object and the light reflected from the reverse side of the same are made to interfere with each other to permit the detection of a flaw.

Namely, in this system, a coherent light is applied to the examination object in the form of a plate having parallel surfaces, and the reverse side of the object is used as the reference mirror while the observe side of the same is being examined. The light internally reflected when the transmitted light passes the reverse side is used as the reference light which is made to interfere with the light reflected from the observe side of the examination object to form an interference pattern.

The first embodiment described before essentially necessitates a reference mirror. The main advantage of the interference type flaw detection method is to provide a high sensitivity of detection. In fact, it is possible to detect with this method even such a small height differential as about 1/40 of the light wavelength (about 0.01 μm). This high sensitivity, on the other hand, requires a delicate adjustment of the reference mirror on the order of the wavelength of light. Also, the interference image is largely changed even by a slight change in the relative position between the reference mirror and the specimen. For instance, the positions of the bright and dark fringes are completely inversed as the relative position is changed in the axial direction by $\frac{1}{4}\cdot\gamma$, i.e. 0.1 to 0.2 μm. This imposes a serious problem particularly when the detection is made automatically. Namely, the play of guiding surface, offset of the rotary shaft and vibration of the driving source are inevitable during the movement of the examination object in the X-Y directions or r-θ directions. In consequence, the interference image is distorted to adversely affect the flaw detection even if the play, offset and vibration are extremely small. In the second embodiment stated above, however, it is possible to obtain the interference image without being affected by the external disturbance such as vibration, because there is no change in the relative position between the examined surface and the reference mirror surface, i.e. the reverse side of the examination object.

In this second embodiment, only an optically transparent object is examined when a visible ray is used as the light from the light source. However, by using a suitable infrared coherent ray such as a semiconductor laser beam, it is possible to obtain an interference pattern even when the examination object is opaque.

The ray 62 emitted from the coherent ray source such as laser beam is made to pass through a beam expander 63 as required to obtain the desired beam diameter, and is focussed upon a first focal point 65 through a first lens 64. Since the ray 62 is generally a parallel light beam, the first focal point 65 coincides with the focal point of the first lens 64. The image on the first focal point 65 is formed on a second focal point 68 by means of a beam splitter 67 and a second lens 66. The second focal point 68 is positioned near the rear focal point of the objective lens 69. By so doing, the ray coming out of the objective lens 69 is changed into a substantially parallel beam having a small diameter which is applied to the examination object 4. On the other hand, the objective lens 69 is adjusted to focus on the surface of the examination object so as to collect the reflected light to form an image on the image surface 7.

From the view point of the light collecting efficiency and easiness of adjustment, it is preferred to use, although not essential, the same kind of lenses for the first lens 64, second lens 66 and the objective lens 69. At the same time, the internally reflected light reflected by the inner surface of the objective lens 69 may appear on the image surface 7 as a background noise to lower the contrast of the interference noise. The background noise, however, can be eliminated by positioning a polarizer 71, quarter wavelength plate 72 and an analyzer 73 at the illustrated positions. Instead of providing the polarizer 71 and the analyzer 73, it is possible to use a polarizing light source as the light source 61, while substituting a polarizing beam splitter for the beam splitter 67. This arrangement permits a more efficient elimination of the noise.

The principle of the interference will be described more fully with reference to FIGS. 11 and 12. As will be understood from FIG. 11, almost the entire portion of the incoming light 76 is transmitted through the surface 34 of the examination object 4 to become transmitted light 79, but a small part of the incoming light is reflected by the surface 74 to become a reflected light 77. The transmitted light is further divided into transmitted light 80 and reflected light 78 as it reaches the reverse side 75 of the examination object 4. The reflected light 78 is emitted again through the surface 74 so that two kinds of reflected light 77 and 78 from an interference on the surface.

Assuming here that the rear focal point 69 of the objective lens perfectly coincides with the second focal point 68, the light 76 coming onto the examination object takes the form of a parallel light beam. In this case, however, an equal condition of interference is obtained at every point on the surface 74 of the examination object 4, so that an image of uniform interference intensity 81, corresponding to FIG. 2, is obtained on the image surface 7. This interference intensity 81 is determined by the thickness 87 of the examination object 4. Namely, representing the thickness 87 of the examination object 4 by $\frac{1}{4}\cdot\lambda\cdot n$, the image is bright when n is an even number and dark when n is an odd number. Therefore, if the obverse side 74 of the examination object 4 and the reverse side 75 of the same are not parallel with each other but inclined to each other, an uneven distribution of the interference intensity is produced in the direction of inclination. This, however, is negligible in the case of usual flat plate, because the range of visible field projected on the image surface is as small as 0.5 mm or so in diameter on the basis of the actual object.

If it is desired to obtain linear interference fringes, it is advisable to employ an arrangement shown in FIG. 12. In this case, the light coming into the examination object 4 is transformed into a slightly converging or diverging light beam. This can easily be achieved by axially displacing the first lens 64 or the second lens 66 in the direction of the optical axis in the arrangement shown in FIG. 10. In FIG. 12, the incoming light is shown as a converging light beam by way of example. Namely, all of the incoming light is focussed on the focal point 85 on the optical axis 84, after having passed through the examination object 4. According to this arrangement, the incident angle of the light coming into the surface 74 of the examination object is nullified, i.e. 0°, on the optical axis but is increased in symmetry with respect to the optical axis, as the radial distance from the optical axis is increased.

In this case, the interference takes place between the light 77 which is the portion 77 of the incoming light reflected by the surface 74, and the portion 78 of the incoming light 82 reflected by the reverse surface 75, the reflected light 78 being located slightly outside of the reflected light 77 with respect to the optical axis. Since the condition for this interference is in symmetry with respect to the optical axis, the interference fringe 86 is formed as concentric circles on the image surface 7. The distance 88 between the fringes is not uniform but is gradually decreased as the radial distance from the optical axis is increased. Insofar as no substantial change of the thickness 87 of the examination object is caused, the number of interference fringes appearing in the image surface 7 can be controlled by adjusting the position of the focal point 85 on the optical axis 84.

Thus, the arrangement shown in FIG. 12 permits the detection of a minute flaw, i.e. a fine projection or recess, existing in the surface of the examination object, in perfectly the same manner as the arrangement explained before in connection with FIG. 8. In this case, however, the flaw detection is influenced more or less by a minute flaw, if any, in the reverse surface of the examination object. This influence, however, is not so serious partly because the objective lens is focussed upon the obverse die of the examination object and partly because the wave surface distorted by the minute flaw in the reverse surface is diverged until it reaches the obverse side of the examination object. Namely, the precision of detection of the minute flaw on the obverse side of the examination object is not affected substantially by the presence of a minute flaw in the reverse surface of the same.

As will be seen from the foregoing description, according to the invention, it is possible to eliminate the problem inevitable in the interference flaw detection method, i.e. the lack of stability against external disturbance, while maintaining the high sensitivity of detection which is the greatest advantage brought about by the method.

What is claimed is:

1. A minute-flaw distinguishing method for distinguishing any minute-flaws existing in the surface of an examination object having a plate-like form comprising the steps of applying a coherent light to the surface of said examination object to make the light reflected by said surface of said examination object and light reflected by a reverse surface of said examination object as a reference mirror surface interfere with each other to form a background image having interference fringes and an interference image of said minute-flaws, transforming said coherent light coming into the examination object into a slightly converging or diverging light beam so as to enable formation of said interference fringes, moving the examination object relative to said slightly converging or diverging beam so as to scan the surface of the examination object with said slightly converging or diverging light beam, and obtaining a high contrast of said interference image of said minute-flaws with respect to said background having said interference fringes so as to enable distinguishing of said minute-flaws.

2. A minute-flaw distinguishing method as claimed in claim 1, wherein the coherent light is infrared.

3. A minute-flaw distinguishing method as claimed in claim 2, wherein said minute-flaws have one of a depth below and a projection above said surface of said examination object smaller than $\frac{1}{4}\lambda$, $\lambda$ being the wavelength of the coherent light.

4. A minute-flaw distinguishing method as claimed in claim 1, wherein said minute-flaws have one of a depth below and a projection above said surface of said examination object smaller than $\frac{1}{4}\lambda$, $\lambda$ being the wavelength of the coherent light.

* * * * *